United States Patent [19]

Engler et al.

[11] 4,089,857
[45] May 16, 1978

[54] TETRATHIAPENTALENE AND TETRASELENAPENTALENE COMPOUNDS

[75] Inventors: Edward Martin Engler, Wappingers Falls, N.Y.; Robert Rhees Schumaker, Los Gatos, Calif.

[73] Assignee: International Business Machines Corporation, Armonk, N.Y.

[21] Appl. No.: 755,891

[22] Filed: Dec. 30, 1976

[51] Int. Cl.² ........................................ C07D 517/04
[52] U.S. Cl. .................. 260/293.56; 260/239 R; 260/293.57; 260/293.63; 260/326.8; 260/326.82; 260/326.83; 260/327 R; 260/455 A; 260/455 B
[58] Field of Search .......... 260/327 R, 239 R, 293.56, 260/293.57, 326.82, 326.8

[56] References Cited

U.S. PATENT DOCUMENTS 4,028,346 7/1977 Engler et al. .................... 260/327 R

OTHER PUBLICATIONS

Bechgaard, K. et al., *J. Chem. Soc. Chem. Comm.,* 937, (1974).
Coffin, D. L., et al., *J. Am. Chem. Soc.,* 93, 2260, (1971).

*Primary Examiner*—Henry R. Jiles
*Assistant Examiner*—Richard A. Schwartz
*Attorney, Agent, or Firm*—Joseph G. Walsh

[57] ABSTRACT

This application is concerned with tetrathiapentalene and tetraselenapentalene compounds. Specifically, it is concerned with 1, 3, 4, 6-tetrathia-2, 5-dihetero-pentalene and 1, 3, 4, 6-tetraselena-2,5-dihetero-pentalene compounds having the formula

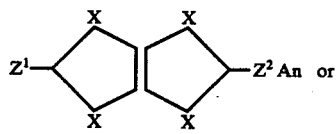

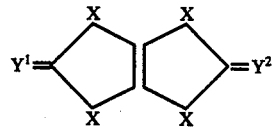

wherein X is S or Se; each of Y¹ and Y² is O, S, or Se; each of Z¹ and Z² is —SR, SeR or

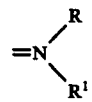

wherein R and R¹ are H, alkyl, aryl, or together form a ring of carbon atoms; and An is the anion of a strong acid. These compounds are key synthetic intermediates for the preparation of tetrathiafulvalene and tetraselenafulvalene materials.

6 Claims, No Drawings

TETRATHIAPENTALENE AND TETRASELENAPENTALENE COMPOUNDS

FIELD OF THE INVENTION

The present disclosure is concerned with the synthesis and properties of novel ring systems, namely, 1, 3, 4, 6-tetrathia-2, 5-dihetero-pentalene, and 1, 3, 4, 6-tetraselena-2, 5-dihetero-pentalene compounds. These compounds are key synthetic intermediates for the preparation of tetrathiafulvalene and tetraselenafulvalene materials.

PRIOR ART

Charge transfer salts containing the organic donors tetrathiafulvalene or its selenium analog tetraselenafulvalene are the most electrically conducting organic solids known (see Coleman et al Sol. St. Commun. 12, 1125 (1973). The tetrathiafulvalene and tetraselenafulvalene compounds of the prior art have the formula:

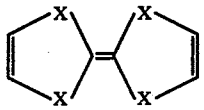

where X is S or Se.

As far as we are aware, no tetrathiapentalene or tetraselenapentalene ring systems have been prepared prior to the present application.

SUMMARY OF THE INVENTION

The overall synthetic procedure for the preparation of compounds of the present invention is outlined below.

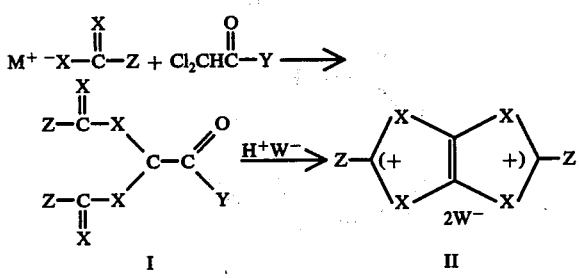

M = alkali (Na$^+$,K$^+$), dialkyl ammonium (e.g., H$_2$N$^+$(CH$_3$)$_2$, piperidinium, etc.)
X = S, Se
Z = N, N-dialkylamine (R$_2$N—), thioalkyl (RS—), oxoalkyl (RO—)
Y = OH, ester (RO—), amide (R$_2$N—), etc.
W = ClO$_4^-$, HSO$_4^-$, BF$_4^-$, PF$_6^-$, etc.

The first step involves the condensation of either an N, N-dialkyl dithiocarbamate or an alkyl di or trithiocarbonate salt (or their selenium analogs) with dichloroacetic acid or its derivatives (e.g., esters, amides, acid chlorides). In the case of esters and amides, two molar equivalents of the dithiocarbamate is required, three molar equivalents for the acid chloride (the acid chloride being replaced during reaction with a dialkyl amide group). The adduct from this reaction (I), a bis-dithiocarbamate (Z = NR$_2$) or a bis- di or trithiocarbonate (Z = SR, OR) derivative, can be cycled by acid treatment (HClO$_4$, H$_2$SO$_4$, etc.) to give 1, 3, 4, 6-tetrathia-2, 5-dihetero-pentalene dication salts (II). In the case where Z above is a oxoalkyl derivative as, for example, that devised from isopropyl alcohol, one obtains directly on acid catalysed cyclization, the diketone having the structure:

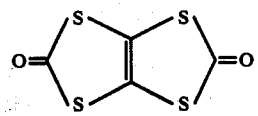

We have found the general reaction sequence described above to work in nearly quantitative yields for a wide variety of derivatives. Some spectroscopic data on a few of the tetrathiapentalene (abbr. as TTP) and tetraselenapentalene (abbr. TSeP) derivatives prepared are summarized in Table I.

TABLE I

| Dication Salt (2W)$^-$ | UV | |
|---|---|---|
| H$_3$C\N$^+$=⟨S-S⟩=$^+$N/CH$_3$ (dimethyl TTP) | 244 | 24,900 |
| piperidinium TTP | 255 | 75,000 |
| piperidinium TSeP | 275 | 55,000 |

Compound II can be converted directly into numerous 2, 6-disubstituted derivatives on addition of various reactants. Active methylene substrates afford neutral species such as

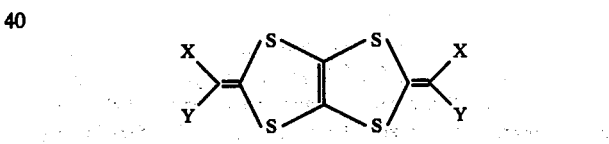

wherein X is —CN, —CO$_2$R, O, —CR, or H and Y is —CN, —CO$_2$R, O, —CR, or NO$_2$.

Compound II also reacts with nucleophiles to yield extended salts such as is shown in the formula:

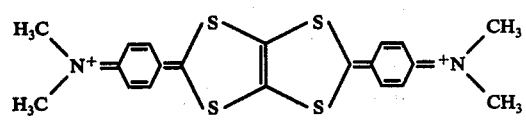

Using established literature procedures, II is capable of being converted into either the dication, having the formula:

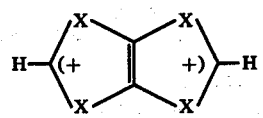

or the dithione (or diselone) derivative, having the formula:

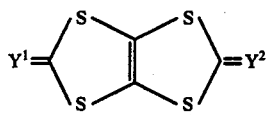

wherein each of $Y^1$ and $Y^2$ is O, S or Se.

The TTP-diketone can be transformed with boron trisulfide into the mixed keto-thione (boiling toluene) or dithione or by mixing and heating in the solid state. Table II lists some properties of these materials:

TABLE II

| Compound | MP. | kr (cm⁻¹) | Analysis (Mole wt.) | uv (λ Max.) |
|---|---|---|---|---|
| $Y^1$ and $Y^1$ are O | 150° d. | 1727 (m) 1678 (s) 973 (w) 914 (w) | Calcd. for $C_4S_4O_2$ 207.878 Found 207.878 | 273 nm 222 |
| $Y^1$ is O $Y^2$ is S | 176–9° d. | 1727 (w) 1700 (m) 1675 (m) 1083 (s) 968 (w) 900 (w) | calcd. for $C_4S_5O_2$ 223.855 Found 223.853 | 390 247 |
| $Y^1$ and $Y^2$ are S | 207–10° d. | 1068 (s) 959 (m) 900 (w) 776 (w) | calcd. for $C_4S_6$ 239.832 Found 239.831 | — |

Reaction of the diketone compound with trimethylphosphite in benzene affords the dimeric diketone, having the formula;

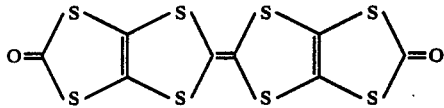

which constitutes an important intermediate for the generation of derivatives of both TTF and TTP, as well as organometallic binuclear and polymeric substances. For example, the diketodimer reacts with ethoxide in ethanol to yield black solutions of the conductive TTF-tetrathia anion salt, having the formula:

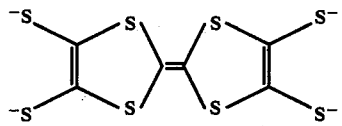

Subsequent addition of methyl iodide leads smoothly to the known tetrathiomethoxy TTF derivative, having the formula:

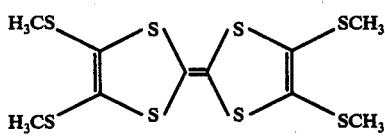

The following examples are given solely for purposes of illustration and are not to be considered limitations on the invention, many variations of which are possible without departing from the spirit or scope thereof.

EXAMPLE 1

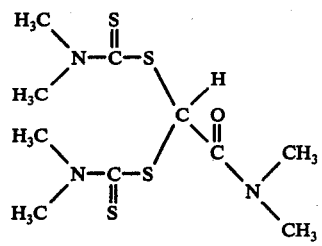

2,2-bis-(N',N'-dimethyldithiocarbamyl)-N,N-dimethylacetamide

To a partially dissolved, magnetically stirred suspension of 27 parts of N,N-dimethyldithiocarbamic acid, sodium salt dihydrate (DMTC-salt), in 700 parts of dioxane is added in one portion 7.5 parts of dichloroacetylchloride. This mixture is heated to reflux temperature for ½ hour and the precipitated sodium chloride is filtered from the hot solution. Dilution of the cooled filtrate with 2,000 parts of n-hexane affords 17 parts of the crude product as a crystalline precipitate containing some tightly bound dioxane. Recrystallization from methanol provides analytically pure 2,2-bis-(N',N'-dimethyldithiocarbamyl) -N,N-dimethylacetamide, mp 225° d., Mol. Wt., calcd., 325.041; found (mass spec.), 325.040.

EXAMPLE 2

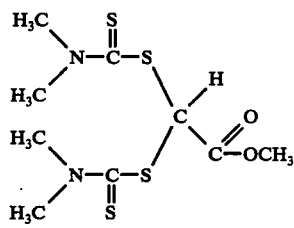

methyl-2,2-bis-(N,N-dimethyldithiocarbamyl) acetate

To a partially dissolved, magnetically stirred suspension of 4.5 parts of DMTC-salt in 200 parts of dioxane was added in one portion 0.36 parts of methyl dichloroacetate and the mixture heated to reflux temperature for ½ hour. The precipitated sodium chloride was filtered from the hot solution and the filtrate diluted with 300 parts of n-hexane affording 5.5 parts of almost pure crystalline methyl 2,2-bis-(N,N-dimethyldithiocarbamyl)-acetate. Methanol recrystallization provides the analytically pure sample, mp 209° d., Mol. Wt., calcd., 312.009; found (mass spec.), 312.010.

Similarly, reaction of either ethyl dibromoacetate or dichloroacetic acid with DMTC-salt affords ethyl-2,2-bis-(N,N-dimethyldithiocarbamyl) acetate, mp 177°; or 2,2-bis N,N-dimethyldithiocarbamyl) acetic acid, mp 149° d.

EXAMPLE 3

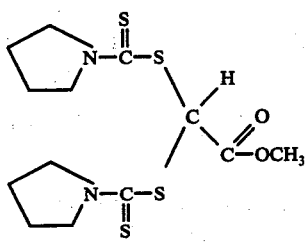

methyl-2,2-bis-(pyrrolidinyldithiocarbamyl) acetate

To 9 parts of pyrrolidinyldithiocarbamic acid, potassium salt in 250 parts of acetone was added 3.5 parts of methyl dichloroacetate and the solution heated to reflux temperature for 1 hour. Sodium chloride was then filtered from the cooled solution and the solvent removed under vacuum to give the crude product as a reddish oil. After washing this oil with cold ether, 6 parts of methyl-2,2-bis-(pyrrolidinyldithiocarbamyl) acetate was obtained by crystallization from an acetone-hexane mixture, mp 162°-4°, Mol. Wt., calcd., 364.042; found (mass spec.), 364.041.

EXAMPLE 4

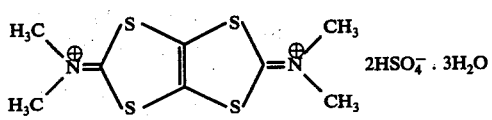

2,5-bis-(N,N-dimethyliminium)-1,3,4,6-tetrathiapentalene disulfate trihydrate or
2,5-bis-(N,N-dimethyliminium) TTP disulfate trihydrate A solution of 5 parts of methyl bis-(N,N-dimethyldithiocarbamyl) acetate in 50 parts concentrated sulfuric acid was warmed for 5 minutes on the steam bath to ensure complete reaction. The cooled solution was then added to 500 parts of ethyl acetate to afford an oily precipitate which crystallized on cooling and scratching. The white crystals obtained were filtered from the solution, washed well with both ethyl acetate and n-hexane and dried under vacuum to yield 5 parts of the hydroscopic 2,5-bis-(N,N-dimethyliminium)-1,3,4,6-tetrathiapentalene [TTP] disulfate salt as the trihydrate, mp 124°-6°.

EXAMPLE 5

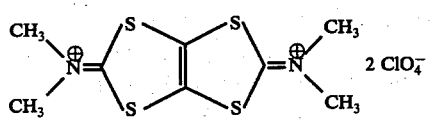

2,5-bis-(N,N-dimethyliminium) TTP diperchlorate

A solution of 1 part of bis-(N',N'-dimethyldithiocarbamyl) N,N-dimethylacetamide in 10 parts of 70% perchloric acid was warmed briefly on the steam bath to ensure reaction. After cooling, the solution was added to 100 parts of ethyl acetate and the colorless crystalline precipitate of 1 part of 2,5-bis-(N,N-dimethyliminium) TTP diperchlorate salt was isolated, mp 170° with detonation. The dried perchlorate salt may detonate violently on touch!

EXAMPLE 6

To 1 part of 2,5-bis-(N,N-dimethyliminium) TTP salt from Example 4 or Example 5 was added 40 parts of absolute ethanol. A transient yellow color is observed and methyl bis-(N,N-dimethyldithiocarbamyl) acetate is precipitated. The mixture was then heated on the steam bath until a clear solution was formed. Ice cooling yielded 0.5 parts of the bis carbamate ester, mp 209°, identical to the ester prepared in Example 2. By this same method, other alcohols provide their corresponding esters of the bis carbamate acid while water treatment yields the acid itself.

EXAMPLE 7

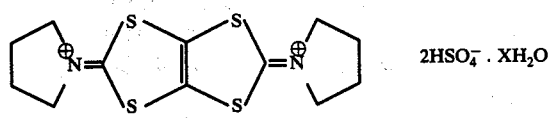

2,5-bis-(pyrrolidinium) TTP disulfate hydrate

A solution of 5 parts of 2,2-bis-(pyrrolidinyldithiocarbamyl) acetate in 50 parts of concentrated sulfuric acid was warmed for 5 minutes on the steam bath to ensure complete reaction. The cooled solution was then added to 500 parts of ethyl acetate to afford a colorless oil. The ethyl acetate was decanted and fresh ethyl acetate added. Prolonged cooling and scratching gave 2,5-bis-(pyrrolidinium) TTP disulfate as a white crystalline hydrate, mp 117°-20° d (closed cap).

EXAMPLE 8

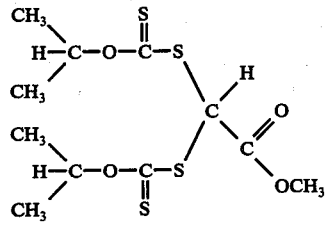

Methyl-2,2-bis-(O-isopropyldithioxanthyl) acetate

To 100 parts of sodium O-isopropyl xanthate suspended in 1700 parts of acetone is added 41 parts of methyl dichloroacetate and the mixture heated briefly to reflux temperature. After cooling, the precipitated sodium chloride is filtered off and the solvent removed under vacuum. The residual oil is taken up in hexane, filtered and the solvent removed to afford methyl 2,2-bis (O-isopropyldithioxanthyl) acetate as a light yellow oil pure enough for further reaction. Ethyl 2,2-bis-(O-ethyldithioxanthyl) acetate was prepared in the same manner from ethyl dibromoacetate and sodium O-ethyl xanthate.

EXAMPLE 9

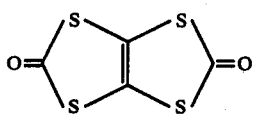

2,5-diketo-1,3,4,6-tetrathiapentalene, or -2,5-diketo TTP

To 10 parts of methyl 2,2-bis-(O-isopropyldithioxanthyl) acetate from Example 8 was added 100 parts of concentrated sulfuric acid slowly while the temperature was maintained at 0°–5° with an ice cooling bath. After the addition, the solution was allowed to warm to room temperature where it was stirred for ½ hour. Pouring the solution on ice then yielded the crude 2,5-diketo TTP as a tacky solid. Crystallization from acetonitrile provides 4 to 5 parts of 2,5-diketo TTP as long white needles, mp 150°, mol. wt. calcd., 207.878; found, (mass spec.), 207.878.

EXAMPLE 10

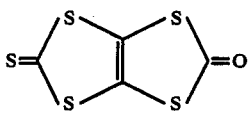

2-keto-5-thionyl-1,3,4,6-tetrathiapentalene or -2-keto-5-thionyl TTP

To 5 parts of 2,5-diketo TTP in 300 parts of toluene is added 19 parts of boron sulfide and the mixture refluxed for 4 hours under a nitrogen atmosphere. The hot solution is filtered and the filtrate evaporated to give the mono-thione admixed with the starting diketone and a trace of the dithione. Chromatography using carbon disulfide elution, gives the pure mono-thione, mp 176°–9°, mol. wt. (Mass spec.) calcd., 223.855; found, 223.853.

EXAMPLE 11

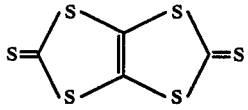

2,5-dithionyl-1,3,4,6-tetrathiapentalene or -2,5-dithionyl TTP

To 5 parts of 2,5-diketo TTP is added 20 parts of boron sulfide and the mixture ground together under a nitrogen atmosphere. The solid mixture is then heated overnight at a temperature of 80°–110°. Extraction of the yellow solids obtained with carbon disulfide gives a solution of 2,5-dithionyl TTP which crystallized on concentration of the solvent, mp 207°–10°, mol. Wt. (mass spec.), calcd., 239.832; found, 239.831.

EXAMPLE 12

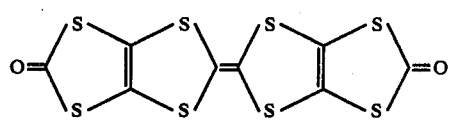

$\Delta^{2,2'}$-bis-(5-keto-1,3,4,6-tetrathiapentalene) or -dimeric diketo TTP

To 4 parts of diketo TTP in 100 parts of dry benzene was added 2 parts of trimethyl phosphite and the solution refluxed under a nitrogen atmosphere overnight. The precipitated 3 parts of dimeric diketo TTP was filtered from the solution and washed well with benzene, mp >360°, analysis, C, 25.19; S, 65.82; O, 8.52%.

EXAMPLE 13

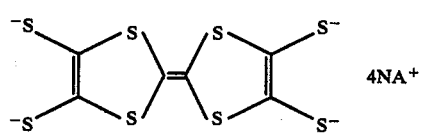

Sodium $\Delta^{2,2'}$-bis-(4,5-dithiolato-1,3-dithiolidene) or sodium tetrathiafulvalene tetrathialate Treatment of dimeric diketo TTP with 4 equivalence of a solution of sodium ethoxide in ethanol under nitrogen at reflux temperature for 2 hours or with 4 equivalence of methyl lithium in tetrahydrofuran at ice temperature for 4 hours generates a dark solution of sodium or lithium tetrathiafulvalene (TTF) tetrathioanion. Addition of methyl iodide to either of these cooled solutions affords high yields of the known tetrathiomethoxy TTF, mp 94°–6°, a conducting derivative of tetrathiafulvalene.

EXAMPLE 14

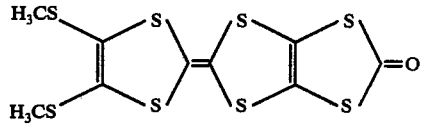

2-keto-5-(4',5'-dithiomethoxy-1',3'-dithioliden-2'-yl) -1,3,4,6-tetrathiapentalene or -2-keto-5-(4',5'-dithiomethoxy-1',3'-dithioliden-2'-yl) TTP Treatment of 1 part dimeric diketo TTP in 250 parts of anhydrous tetrahydrofuran with 2 equivalence of methyl lithium (1.45 M in ether) at ice temperature for 2 hours followed by the addition of 3 parts methyl iodide gives a solution from which is obtained by chromatography on silica gel, 2-keto-5-(4',5'-dithiomethoxy-1',3'-dithioliden-2-yl) TTP; mp 178° d., mol. wt. (mass spec.), calcd., 385.818; 385.819.

EXAMPLE 15

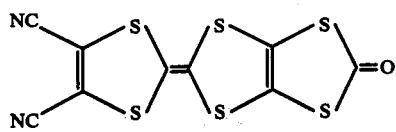

2-keto-5-(4',5'-dicyano-1',3'-dithioliden-2'-yl)-1,3,4,6-tetrathiapentalene or
-2-keto-5-(4',5'-dicyano-1',3'-dithioliden-2'-yl) TTP

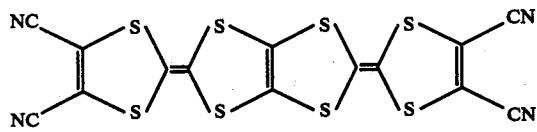

2,5-bis-(4',5'-dicyano-1',3'-dithioliden-2'-yl) TTP

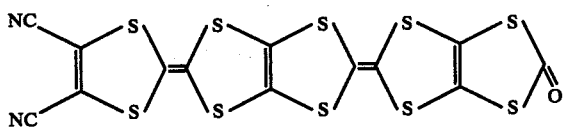

5-(4',5'-dicyano-1,3'-dithioliden-2'-yl)-2-(2'-keto-1',3',4',6'-tetrathiapentalen-5'-yl) TTP To 5 parts of 2,5-diketo TTP and 4 parts of 4,5-dicyano-1,3-dithiovinylene carbonate is added 4 parts of trimethylphosphite and the solution heated to reflux temperature under a nitrogen atmosphere for 4 hours. The solution is cooled overnight and the crystalline material (mainly tetracyano TTF) is filtered off. The mother liquor is then chromatographed on silica gel to afford on elution with a 50% benzene-hexane mixture, 0.5 parts of 2-keto-5-(4',5'-dicyano-1', 3'-dithioliden-2'-yl) TTP, mp 196° d., mol. wt. (mass spec.), calcd., 343.833; found, 343.835 which recrystallizes from acetonitrile as ruby-red platelets.

From the initial crystalline material is isolated by extracting away the tetracyano TTF, small amounts of 2,5-bis-(4',5'-dicyano-1',3'-dithioliden-2'-yl) TTP as a metallic-gray powder which crystallizes from methylene chloride, mp 290° d. and 5-(4',5'-dicyano-1',3'-dithioliden-2'-yl)-2-(2'-keto-1',3',4',6'-tetrathiapentalen-5'-yl) TTP as dark-red crystals, mp >360°. The latter two compounds are the first known instances of two tetrathiafulvalene molecules fused together.

EXAMPLE 16

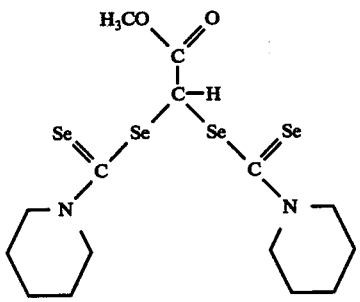

methyl-2,2-bis-(N,N-pentamethylenediselenocarbamyl) acetate

To 6.8 parts of N,N-pentamethylenediselenocarbamic acid piperidine salt suspended in 200 parts of methylene chloride, was added 1.4 parts of methyl dichloroacetate and the mixture stirred for 4 hours at room temperature. After dilution with 400 parts of ether and filtration of precipitated salt, the solution was washed five times with water, dried over sodium sulfate and the solvent removed to give the crude product. Crystallization from a hexane-chloroform mixture or from methylcyclohexane yielded pure methyl-2,2-bis-(N,N-pentamethylenediselenocarbamyl) acetate as yellow-orange needles; mp 150°–51°; analysis: C, 30.86; H, 4.29; N, 4.68; Se, 54.30%.

EXAMPLE 17

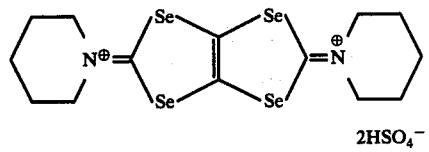

2,5-bis-(piperidinium)-1,3,4,6-tetraselenapentalene disulfate salt

Dissolving 1 part of methyl-2,2-bis-(N,N-pentamethylenediselenocarbamyl) acetate from Example 16 in 10 parts of concentrated sulfuric acid and precipitation with 100 parts of ethyl acetate afforded white crystals of 2,5-bis-(piperidinium)-1,3,4,6-tetraselenapentalene disulfate salt.

What is claimed is:

1. 1, 3, 4, 6-tetrathia-2, 5-diheteropentalene and 1, 3, 4, 6-tetraselena-2, 5-dihetero-pentalene compounds having the formula:

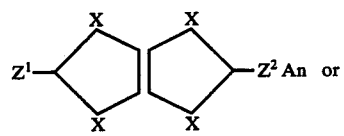

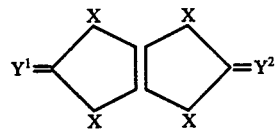

wherein X is S or Se; each of $Y^1$ and $Y^2$ is O, S, or Se; each of $Z^1$ and $Z^2$ is —SR, SeR or

wherein R and $R^1$ are H, lower alkyl, phenyl, or taken together with the N form a piperidine or pyrrolidine ring, and An is the anion of a strong acid.

2. 2,5-bis-(N,N-dimethyliminium)-1,3,4,6-tetrathiapentalene salts of strong acids having the formula:

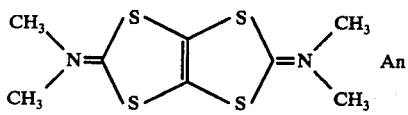

wherein An is the anion of a strong acid.

3. 2,5-bis-(piperidinium-1,3,4,6-tetraselenapentalene salts of strong acids having the formula:

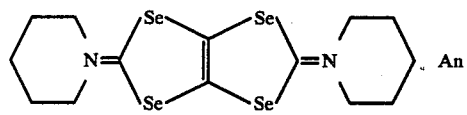

wherein An is the anion of a strong acid.

4. 2,5-diketo-1,3,4,6-tetrathiapentalene having the formula:

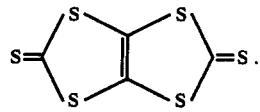

5. 2,5-dithionyl-1,3,4,6-tetrathiapentalene having the formula:

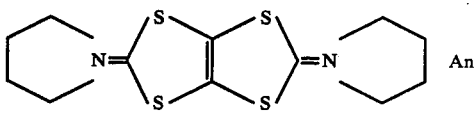

6. 2,5-bis-(pyrrolidinium) tetrathiapentalene salts of strong acids having the formula:

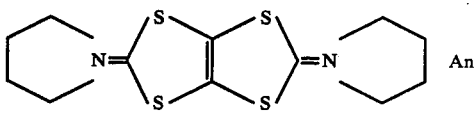

wherein An is the anion of a strong acid.

* * * * *